United States Patent [19]

Philippe et al.

[11] Patent Number: 4,820,299
[45] Date of Patent: Apr. 11, 1989

[54] PROSTHETIC CARDIAC VALVE

[75] Inventors: Perrier Philippe, St. Nom-la-Bretecne; Lapeyre Didier, Chaignes, both of France

[73] Assignee: Avions Marcel Dassault-Breguet Aviation, Vaucresson, France; a part interest

[21] Appl. No.: 910,621

[22] Filed: Sep. 23, 1986

[30] Foreign Application Priority Data

Sep. 23, 1985 [FR] France ............... 85 14051

[51] Int. Cl.⁴ .................................. A61F 2/24
[52] U.S. Cl. ........................................ 623/2
[58] Field of Search ............................ 623/2

[56] References Cited

U.S. PATENT DOCUMENTS

| 3,938,197 | 2/1976 | Milo | 623/2 |
|---|---|---|---|
| 4,078,268 | 3/1978 | Possis | 623/2 |
| 4,363,142 | 12/1982 | Meyer | 623/2 |

FOREIGN PATENT DOCUMENTS 1503297 11/1967 France .
WO82/03981 11/1982 PCT Int'l Appl. .
2051308 1/1981 United Kingdom .

Primary Examiner—Richard J. Apley
Assistant Examiner—James Prizant
Attorney, Agent, or Firm—Oblon, Fisher, Spivak, McClelland & Maier

[57] ABSTRACT

A prosthetic cardiac valve with a plurality of flaps supported by a base through a rotational guide and retaining mechanism between an open position and a closed position.

The valve is characterized in that:

the guide and retaining mechaism define a virtual axis of rotation disposed at a distance from the axis of the valve which is greater than 75% of the radius of the base measured along the axis of symmetry of a flap, each virtual axis, situated outside the corresponding flap, is offcentered with respect to the center of gravity of the flap, and in the open position, the corners of each flap come to bear on the internal wall of the base in zones which are situated at a distance from the corresponding virtual axis of rotation which is greater than 25% of the radius of the base.

21 Claims, 11 Drawing Sheets

PROSTHETIC CARDIAC VALVE

BACKGROUND OF THE INVENTION

1. Field of the Invention

The present invention relates to a prosthetic cardiac valve intended to be implanted in a human being for replacing a natural cardiac value which has been damaged or functions badly.

2. Description of the Prior Art

Several cardiac valve prostheses have been proposed in the Prior Art. In the work by E.A. LEFRAK and A. STARR, edited in 1979 by Appleton-Century-Crofts, New York, and entitled: "Cardiac valve prostheses", there are presented the historical, hemodynamic and clinical aspects of different mechanical and biological prosthetic cardiac valves. Among the mechanical cardiac values (to which our analysis of the Prior Art refers, because biological prothetic valves dapart from the scope of the invention), there will only be recalled here some solutions comprising at least two flaps letting the blood flow in one direction and preventing it from flowing in the opposite direction.

The American patent S. MILO No. 3 938 197, describes an artificial cardiac value with central flow, namely having the central zone completely cleared in the open position. This value comprises a plurality of flaps, more particularly five, which have a substantially triangular shape and whose lower face is concave over about the lower 4/5 of its height, whereas it is convex over about the upper 1/5 of said height, which flaps are each hinged about a peripheral segment formed by the male/female assembly of two elements, which assembly is stabilized by means of a screw which is fitted into a peripheral hole formed in an element parallel to the pivoting axis of the corresponding flap and which is screwed into the other element.

The American patent Z. C. POSSIS No. 4 078 268 describes a prosthetic cardiac valve with, in a first embodiment, two flaps each pivoting about a shaft integral with the corresponding flap and formed by two shaft projections disposed on the lateral sides of the valve at a distance from its leading edge equal to ⅓ of the height of the value, the rotational movement of each flap being limited by appropriate projections projecting from the supporting rim (or base or body) of the flaps, towards the central passage of the valve.

In a second embodiment, the above POSSIS patent describes valves whose rotational movement between the closed and open positions and vice-versa is provided, under the action of the cardiac pulsation, by pivoting and stop means each having two pairs of projections which project slightly from the annular base or housing of the valve towards the central passage and which define together a virtual axis of rotation. Each pair of projections is formed by an upper projection having a pivot portion and a substantially vertical stop face and by a lower projection slightly offset with respect to the upper portion and it is also provided with a pivot portion and a stop face inclined inwardly and upwardly. Each valve is included between two pairs of projections, the upper projection of which cooperates with a lateral lug projecting from the upper face of the corresponding valve and disposed below with respect to said upper projection.

Insofar as the support base for the flaps described in the POSSIS patent is concerned, it is formed by screwing or fitting/clipping an internal portion in an external portion, the internal portion being possibly formed by two semi-circular segments in the case where the assembly is provided by fitting/clipping together.

In addition, the distance of each of the two real or virtual axes of rotation, with respect to the axis of the valve, is between about 75% and 65% of the radius of the central passage defined by the support base, so that this latter is amply freed without however being optimally freed.

The French patent CARPENTIER No. 2 331 997, corresponding to the American patent No. 4 159 543, describes a prosthetic cardiac valve of the type including a substantially circular support base having at least one seat and two substantially semi-circular movable flaps adapted to rest on the seat.

Each flap of the CARPENTIER valve cooperates with means allowing the translational and rotational movements of the two flaps, and particularly the rotation through an angle less than 90°, and translation parallel to the axis of the support base. The roto-translational means are formed, for each flap, by a transverse shaft disposed in the vicinity of a diameter of the base and by pegs, particularly in the form of shaped ridges, disposed alternately on each side with respect to the corresponding shaft and projecting from the external face of the valve. The translational movement is provided by the fact that, when the valve is considered in the closed position and therefore with each flap resting of the corresponding seat, between the shaft of rotation and the external face of the flap, there exists a certain distance, which prevents the permanent contact between each flap and the corresponding shaft.

There are also known from the French patent application No. 2 543 429, in the name of UNIVERSITE PIERRE ET MARIE CURIE and having again as inventor M. CARPENTIER, some improvements which are brought about the very prosthetic cardiac valve described in the above CARPENTIER French patent No. 2 331 997: it is a question of providing each flap, and/or the corresponding seat of the valve, of a device known per se, capable of ensuring controlled opening of the valve when the blood pressure is balanced on both the internal and external faces of the mobile flap; that means that, under these conditions of pressure balance, the valve is slightly open. The device, known per se, proposed by CARPENTIER for controlling the opening of the valve is formed, for each flap, by two magnets or electro-magnets one of which is disposed on the flap whereas the other is disposed on the corresponding seat. Alternately, this device may be formed by a spring fixed to the seat.

Furthermore, the American patent No. 4,276,658 D. W. HANSON et al, corresponding to French patent No. 2 407 709, describes a cardiac valve prosthesis of the type having a body with a central passage for blood flow, means for adjusting this flow, which pivot under the action of the blood flow between a closed position and an open position, and means for hinging these adjustment means. The HANSON et al valve includes hinging means having cavities formed in said body and with a bearing surface in the form of a surface of revolution and adjustment means provided with projections for penetrating into the cavities and sweeping the (abutment) surface with the end which is in contact with this surface.

The American patent L. C. MEYER, No. 3 589 392, is also known which describes an artificial cardiac valve whose flaps have a concave internal face (substantially in the form of a spoon) and are hinged (pivoted) about a flexible arcuate portion which is supported by the base of the valve; however, the MEYER valve has a dimension in height which is exaggerately large, which is due particularly to the design of the pivot means used for the flaps.

Apart from the MEYER valve for the above reasons, and in particular because it is not a valve of the so-called "low profile" type, it is clear that each of the prosthetic cardiac valves of the Prior Art have advantages and disadvantages which are proper thereto, particularly:

insofar as the MILO valve is concerned, though on the one hand it provides a central flow for the blood, on the other hand it has zones of stagnation of the blood under said peripheral hinging segments of the flaps, namely that the cellular elements of the blood tend to remain confined under these segments, which produces a beginning of coagulation and therefore, in the long run, thrombosis effects;

in so far as the POSSIS valve is concerned, although it eliminates the problems of stagnation of the blood occurring in the MILO valve, however the central blood flow passage is not yet freed to the maximum of the possibilities and the flaps are slanted towards the valve axis, in the open position, so that the problems of turbulence—even though they are reduced—are still considerable; furthermore, the constructive solution of the support base for the flaps formed of several elements presents the potential risk of separation of these elements and of the formation of blood stagnation zones;

insofar as the CARPENTIER valve is concerned, described in the French patent No. 2 331 997, although it avoids the formation of permanent contacts between the fixed parts and the movable parts of the prosthesis and so reduces the formation of clots, on the other hand the substantially central position of the flaps and their relatively considerable slant with respect to the vertical are sources of turbulences in the central part of the flow, which turbulences are all the greater and more troublesome since the flow is faster at this position, so that the preceding advantage is practically cancelled out and the risks of coagulation exist also in this case;

insofar as the CARPENTIER valve is concerned described in the French patent No. 2 543 429, it should be emphasized that it privileges the performances at opening time, whereas, in practice, it is rather the behavior of the valve at closing time which raises problems, particularly due to the blood regurgitation during the return of the blood flow in the reverse direction;

insofar as the HANSON et al valve is concerned, the harmful effects (crushing and so destruction) on the red corpuscles of the blood still remain considerable because of the friction action between said projections of the flaps and said cavities housing these projections.

Furthermore, in a general way, the design of all the prosthetic valves of the Prior Art is such that the hinging means are subjected to very high forces which are responsible for the premature wear of the existing valves. An object of the present invention is therefore to provide a prosthetic valve whose hinge means are subjected only to low forces, thus taking care of a vital aspect in the design of cardiac valve protheses, as is rightly emphasized by the surgeon D. LIOTTA of the HOSPITAL ITALIANO of Buenos Aires, in Argentina, on page 49 of the TEXAS HEART INSTITUTE JOURNAL, vol 12 No. 1 of March, 1985.

SUMMARY OF THE INVENTION

Another object of the present invention is to provide a prosthetic cardiac valve which answers better the requirements of practice than the previously known cardiac valve prostheses, particularly in that:

In the open position:
the disturbance (turbulence) of the blood flow in the forward direction is the lowest possible;
the pressure charge losses are minimum;
the friction charge losses are also minimized;
the valve closure means (flaps), because of their arrangement substantially parallel to the flow, are not subjected or are only subjected in a lesser degree to the pressure forces, which avoids the creation of vortices in the vicinity of the flaps;
the local mechanical stresses and the wear are limited to a great extent because the higher forces are distributed over the solid portions of the valve (support base and flaps) whose wear is generally very low;
the operating noise is substantially reduced,
the closure of the valve closure means may be anticipated on the return of the blood flow, which minimizes the problems of regurgitation;
the stresses acting on the retaining (stop) means of the flaps are not amplified by a lever effect;
opening of the closure means takes place naturally as soon as there exists a pressure gradient in the forward direction;
in the closed position the blood leak is reduced to a minimum;
the height of the flaps and the projection in the open position of these latter with respect to the base are as low as possible ("low profile valve");
the central blood flow passage has a section which is larger than the free section of existing valves;
the absence of stagnation zones allows efficient rinsing at each cycle of all the parts of the valve and in particular the hinge means.

The present invention provides a prosthetic cardiac valve of the type including:

a plurality of closure means (or flaps) having a concave internal face and being movable, under the action of the heart pulsations, between an open position in which they allow the blood to flow in one direction, called a forward direction, and a closed position in which they prevent the reversal of the blood flow in the opposite direction, called a reverse direction, each closure means including two lateral corners, a leading edge and a trailing edge which converge in these two corners;

a base supporting the closure means having an internal wall defining a central passage for the blood flow, as well as an upper edge and a lower edge;

suture means by means of which the base is fixed to the heart and vascular tissues, and rotational guidance and retaining means for each closure means between and in said two open and closed positions, respectively, when valve is characterized:

in that the guide and retaining means for each flap define a virtual axis of rotation disposed at a distance from the axis of the valve which is greater than 75% of the internal radius of the base measured along the axis of symmetry of a flap, while allowing the flow between the external face of the corresponding flap and the internal wall of the base and so efficient rinsing of said guide and retaining means;

in that each virtual axis is situated entirely outside the corresponding flap and is sufficiently off-centered with respect to the centre of gravity of the flap so that the resultant of the friction forces acting on the flap have, with respect to said virtual axis during reversal of the blood flow, a sufficient moment for causing closure of the corresponding flap, and in that, in the open position, the corners of each flap come to bear—through a portion included substantially, in said open position, between the upper edge of the base and the leading edge of each flap—on the internal wall of the base at zones which are situated at a distance from the corresponding virtual axis of rotation which is greater than 25% of said radius of the base measured along the axis of symmetry of a flap or perpendicular to the rotation axis of the flap, which reduces the forces required for limiting the opening of the flap and reduces the forces urging the guide means to rotate.

In a preferred embodiment of the prosthetic cardiac valve of the invention, said rotational guide and retaining means for each flap are formed by:

a first spur which projects from the external face of the corresponding flap outwardly and upwardly from the middle point of its leading edge;

a means about which the first spur is hinged and which is integral with the internal wall of the base; and a second and a third spur which project substantially from the lower edge of the base and which are oriented towards the axis of the base, namely the flow axis, and slightly upwardly, said second and third spurs being disposed on each side with respect to the hinge means of said first spur and coming into contact with the leading edge and the lower zone of the internal face of the corresponding flap, respectively in the open and closed positions.

In a preferred arrangement of this embodment, said hinge means of said first spur is formed by a substantially horizontal and preferably substantially triangular stirrup which projects from the internal wall of the base and which is disposed in the lower half of this wall, in the vicinity of the median radial plane of the base, which stirrup has a radial width less than 25% of the radius of the base measured along the axis of symmetry of a flap or perpendicular to the rotation axis.

In an advantageous variant of this arrangement, said hinge means of the first spur is formed by two substantially horizontal spurs which project from the internal wall of the base and converge towards each other, the free ends of these convergent spurs being slightly spaced apart and spaced from the internal wall of the base by a radial distance less than 25% of the radius of the base measured along the axis of symmetry of a flap or perpendicular to the rotation axis.

In a preferred embodiment of the valve of the invention, the radial dimension of said hinge means of the first spur is preferably between 10% and 15% of the radius of the base measured along the axis of symmetry of a flap.

In another preferred embodiment of the valve of the invention, in the open position, each flap is substantially parallel to the blood flow axis, namely the internal and external faces of each flap are lightly touched by the blood substantially parallel to the axis of the base.

In the advantageous embodiment of the valve of the invention, the internal wall of the base has in axial section a curvilinear profile which includes a concave upper portion, along which the thickness of said internal wall increases from the upper edge of the base and a convex lower portion along which the thickness of the internal wall decreases towards the lower edge of the base, said concave and convex portions of the axial profile of the internal wall of the base being separated by an annular line.

In another advantageous embodiment of the valve of the invention, the line of separation between said concave and convex portions of said axial profile of the internal wall of the base varies, in the zone between two adjacent flaps, along a radial profile which projects with respect to the radial profile of the median zone of the flap and which is substantially symmetrical with respect to the trailing edges of two adjacent flaps touching each other in the closed position, the leading edge of each flap having in its turn a profile matching the line of separation between said concave and convex portions of the profile of the internal wall of the base, namely the leading edge of each flap has a convex central portion and two lateral reentrant portions, these latter matching, in the closed position, said projecting radial profile of the internal wall of the valve, matching in the closed position between the leading edge of each flap and the internal wall of the base being provided so as to reduce the blood leaks to a minimum.

In an advantageous arrangement of this embodiment, the portion of said line of separation between said concave and convex portions of the axial profile of the internal wall of the base, which corresponds to the convex portion of the leading edge of each flap, is situated at a distance from the lower edge of the base which is equal to about 10% of the height of this base, whereas the middle point of the portion of said line of separation with projecting radial profile which corresponds to the two concave portions of two adjacent flaps, is situated at a distance from the lower edge of the base which is equal to about 20% of its height, the passage between said two portions of said line of separation being progressive.

In another advantageous embodiment of the valve of the invention, each flap has at the level of its corners, which come into contact with the internal wall of the base in the closed position, and on its external face, a reinforcing thickening thus allowing the contact to be made over a surface and not by a point or a line, thus limiting the contact pressure and so the wear, as well as the operating noise.

In another embodiment of the valve of the invention, each of the flaps is provided with closure advance means, namely means for anticipating closure of the flaps on the return of the blood flow in the opposite direction, which cooperate with the closure starting means formed by said virtual offcentered axes.

In a preferred arrangement of this embodiment, said closure advance means are formed by magnetic masses having opposite polarities formed at the level of the corners of each flap, the magnetic polarities of the corners of two adjacent flaps being opposite.

In an advantageous mode of this arrangement, said magnetic masses are formed by small magnets.

In an advantageous variant of said mode, said magnetic masses are formed by a magnetic material incorporated during the manufacture of each flap.

In another advantageous embodiment of the valve of the invention, the number of flaps is equal to 2.

In a preferred variant of this embodiment, the number of flaps is greater than 2.

In an advantageous arrangement of this variant, the number of flaps is preferably equal to 3.

BRIEF DESCRIPTION OF THE DRAWINGS

Besides the above arrangements, the invention includes further arrangements which will be clear from the following description.

The invention will be better understood from the complement of description which follows with reference to the accompanying drawings in which.

It should however be understood that these drawings and the corresponding descriptive parts are given solely by way of illustration of the object of the invention, of which they in no wise form a limitation.

DESCRIPTION OF THE PREFERRED EMBODIMENTS

The cardiac valve prosthesis includes an annular base 2 with a passage 3 for the flow of the blood under the action of the cardiac pulsations, this passage being defined by an internal wall 4 whose precise configuration will be described hereafter.

This base 2 also includes two annular collars 23 and 24 projecting from its lower 28a and upper 28b edges and defining a groove intended to receive suture means (not shown), known per se, for fixing the valve to the cardiac and vascular tissues.

The blood flow is controlled by three closure means 5, 6 and 7 formed by flaps defined by a leading edge 8 having a convex central portion 8a and two concave lateral portions 8b and a trailing edge 9. Each flap has an internal concavity defined by a substantially flat central portion 10 and two arcuate side portions (or corners) 11 and 12. In this case, the trailing edge 9 is in the form of an inverted V with curvilinear arms 13 and 14 so that the flaps having a substantially triangular shape with an apex 15. It is obvious that this condition is verified from a number of flaps equal to or greater than 3, whereas in the case of two flaps the trailing edge would, when they are considered in the completely open position, be horizontal and curvilinear following the concavity of each flap.

Figure 4:
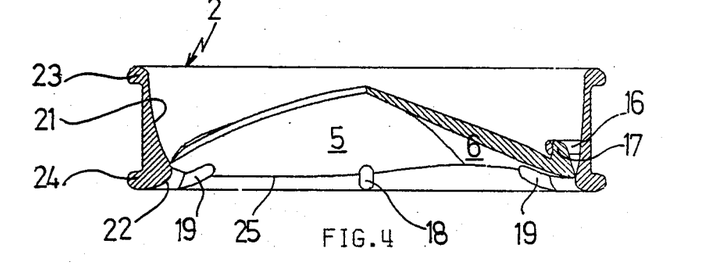
FIG. 4 is a sectional view through the plane IV of FIG. 1.
Figure 5:
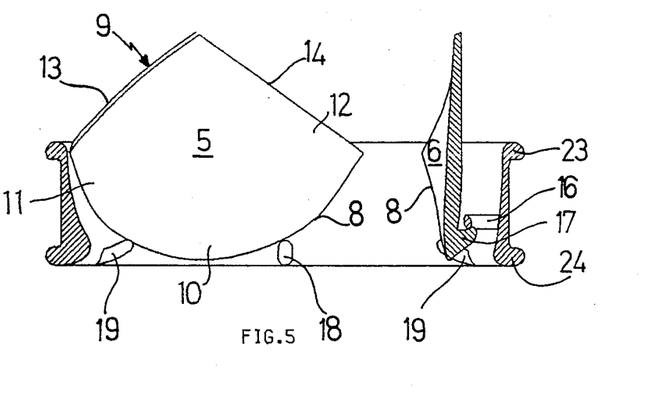
FIG. 5 is a sectional view through the plane V of FIG. 3.
Figures 6, 6A:
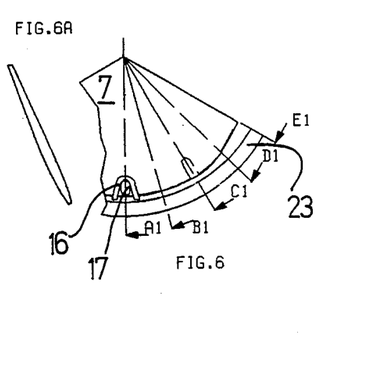
FIGS. 6a to 6e are sectional views of a flap of the valve of the invention which show how the profile of each flap varies from the axis of the flap towards one or other of its corners and in the radial direction, such as defined by the sectional planes $A_1$, $B_1$, $C_1$, $D_1$ and $E_1$ of FIG. 6.
Figures 6B, 6C:
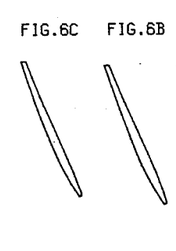
Figures 6D, 6E:
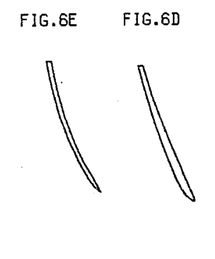
Figure 7:
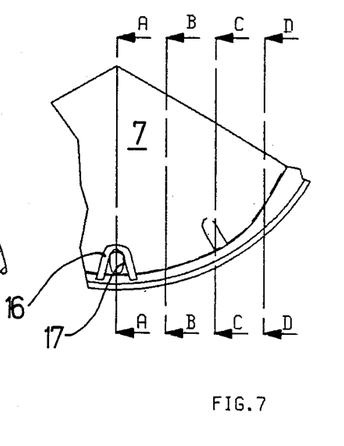
FIGS. 7a to 7d are sectional views similar to those of FIGS. 6a to 6e which show how the profile of each flap varies from the axis of the flap towards one or other of its corners and parallel to this axis, such as defined by the sectional planes $A_2$, $B_2$, $C_2$ and $D_2$, FIG. 7
Figures 7A, 7B, 7C, 7D:
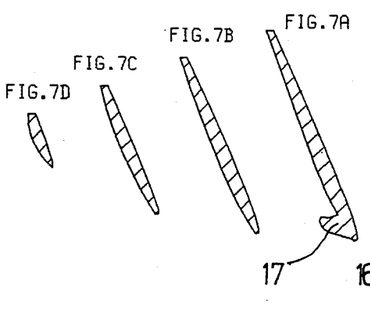

The three flaps 5, 6 and 7 are mobile between an open position (cf. FIGS. 3, 3a and 5), in which they allow the blood to flow in one direction, called a forward direction, and a closed position (cf. FIGS. 1, 1a and 4) in which they prevent the reversal of the blood flow in the opposite direction, called a reverse direction.

The movement of the three flaps takes place under the action of the cardiac pulsations through the presence of rotational guidance and retaining means.

According to the invention, these guidance and retaining means are formed by a substantially horizontal and triangular stirrup 16 which projects from the internal wall 4 of base 2 and which is disposed in the lower half of this wall close to the median radial plane of the base (cf; in particular FIG. 5) and by three spurs.

A first spur 17 projects from the external face of a flap outwardly and upwardly (cf. again in particular FIG. 5) from the middle point of the leading edge; this spur 17 cooperates with said stirrup 16 which is thus disposed on the external face side of the flap.

The second and third spurs 18 and 19 project from the lower edge of base 2 and are oriented towards the axis of the valve (by asis of the valve is meant the axis of the cylinder of revolution having the largest radius which may be inscribed inside the base) and slightly upwardly, these two spurs 18,19 being disposed each on one side of said stirrup 16 and so of said first spur 17, and they come into contact with the leading edge of the corresponding flap in the open position.

It goes without saying that the relative arrangement between said stirrup 16 and said spurs 17, 18 and 19 may be reversed without the operation of the valve being compromised, however the arrangement shown is that which is preferred without the scope of the present invention.

Furthermore, it is also obvious that stirrup 16 may also be rectangular, and it may be advantageous—while keeping the substantially triangular configuration—to form it open at the level of its apex, in this case being formed by two substantially horizontal convergent spurs (not shown) whose free ends are slightly spaced apart.

In each case, the stirrup 16 and the spurs 17, 18 and 19 are dimensioned and positioned so that in the open position each of the three flaps 5, 6 and 7 is disposed in the vicinity of the internal wall 4 of the base 2, the radial dimension of the stirrup 16 being less than 25% of the radius of the base and, preferably, between 10% and 15% of this radius, which provides a flow section for the blood which has never been equalled in the prior art valves.

It can then be seen that the valve of the invention includes means for guiding and retaining each flap which define a virtual axis of rotation disposed at a distance from the axis of the valve which is greater than 75% of the radius of the base 2 measured along the axis of symmetry of a flap, while allowing flow between the external face of the corresponding flap and the internal wall of the base and so efficient rinsing of the guide and retaining means.

Furthermore, it may be noted that each virtual axis is situated entirely outside the corresponding flap and is sufficiently offcentered with respect to the center of gravity of the flap so that the resultant of the friction forces acting on the flap have, with respect to said virtual axis at the time of reversal of the blood flow, a sufficient moment for starting the closing movement of the corresponding flap: it is this offcentered arrangement of the axes of rotation of the flaps which allows the flaps to be placed, in the open position, substantially parallel to the axis of the blood flow, for the friction forces alone are sufficient for providing closure thereof and, therefore, the pressure forces are not required for this purpose. (In this connection, it should be noted that in the prior art the closure of the flaps occurs under the effect of the pressure forces alone).

Furthermore, the arrangement of the guide and retainer means is particularly advantageous because the flaps are disposed very close to the internal wall of the base, namely they are situated in a zone where the flow is slowed down by the proximity effect of the wall, which considerably reduces the charge losses due to the presence of the flaps. Moreover, the slant of spurs 18 and 19 is such that, in the open position, the internal face of the flaps is substantially parallel to the axis of the valve (axis of the base), with the line joining the two corners 11 and 12 of the flaps substantially perpendicular to this axis. The parallelism between the axis of the valve (and so the forward flow direction of the blood) and each flap in the open position, together with their substantially peripheral arrangement, eliminates the problems of turbulence arising in the prior art valves due to the slant of the flaps with respect to the axis of the blood flow.

Now, in the open position, the corners 11 and 12 of each flap come to bear on the internal wall of the base at the zones which are situated at a distance from the corresponding virtual axis of rotation which is greater than 25% of the radius of the base (still measured along the axis of symmetry of a flap or perpendicular to the rotation axis): thus, the forces required for limiting the opening of the flaps are reduced as well as the forces acting on the rotational guide and retainer means of these flaps.

In the closed position, it may be noted (cf. FIG. 1) that each leading edge includes a convex central portion 8a and two concave lateral portions 8b disposed at the level of the corners 11 and 12 of each flap and matching the profile of the internal wall of the base. The profile of this wall includes, in axial section, a concave upper portion 21 of increasing thickness and a convex lower portion 22 of decreasing thickness. The line of separation 25 between these two portions 21 and 22 may advantageously have, between two adjacent flaps, a convex and substantially symmetrical radial profile 26 between two setback portions 27.

The profile of the internal wall of the base and of the leading edge, which is matched thereto, ensures the retention of the flaps in the closed position, their matching being such that the blood leaks are minimized.

Figure 1:
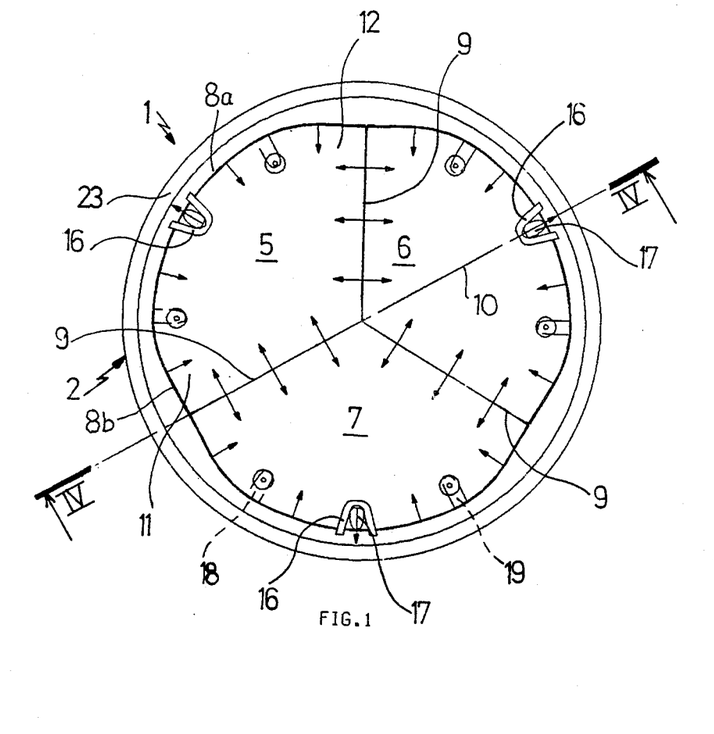
FIGS. 1 and 1a are top and perspective views respectively of the cardiac valve prosthesis of the invention in the closed position.
Figure 1A:
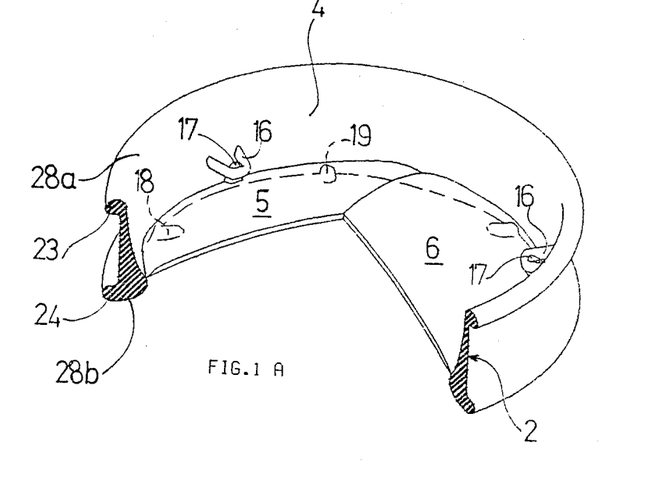
Figure 3:
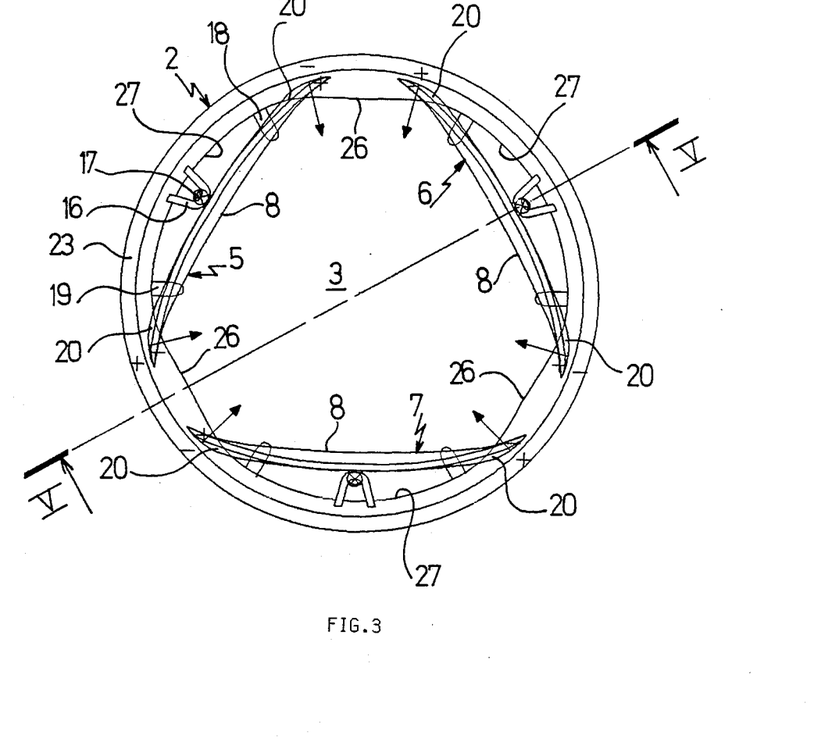
FIGS. 3 and 3a are views also from the top and in perspective, respectively, of the preceding valve in the completely open position, the perspective FIGS. 1a, 2a, 3a being shown with parts cut away.

FIGS. 1 and 3 show the distribution of the retaining forces in the two closed and open positions respectively, which is schematically illustrated by arrows and small circles containing a dot or a cross. Now, since the highest retaining forces appear in the closed position, it is advantageous, so as to limit the wear, to distribute them uniformly, which is obtained by the contact of the flaps with each other along with their trailing edges and with the internal wall of the base along their leading edges.

For limiting the local stresses and so the wear, also in the open position, valves 5, 6 and 7 have on the external face a thicknenng 20 of the corners 11 and 12 (cf. FIG. 3) intended to reinforce this bearing zone on the base and to increase the bearing surface so as to reduce the abutment pressures and, at the same time, the operating noise.

With the preceding arrangements, the highest operating forces are therefore distributed over the solid parts of the valve (base and flaps) whose wear is low.

The valve of the present invention is provided with closure advance means, namely means intended to anticipate closure of the flaps on the return of the blood flow in the opposite direction, and thus to minimize the problem of regurgitation, which means cooperate with the closure starting means which are defined by the off-centered arrangement of the virtual axis of rotation of each flap with respect to the corresponding flap.

Figure 2:
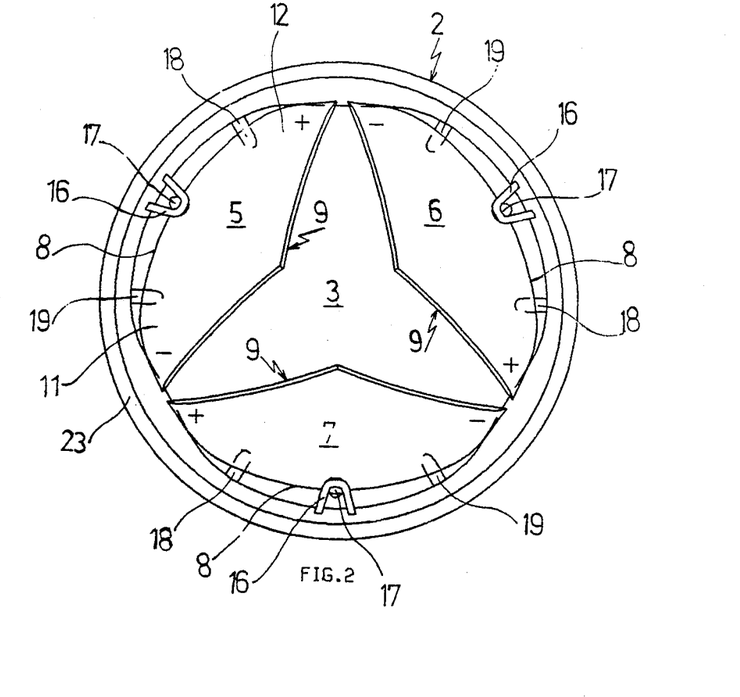
FIGS. 2 and 2a are views also from the top and in perspective, respectively, of the valve shown in FIGS. 1 and 1a but in the partially open position.
Figure 2A:
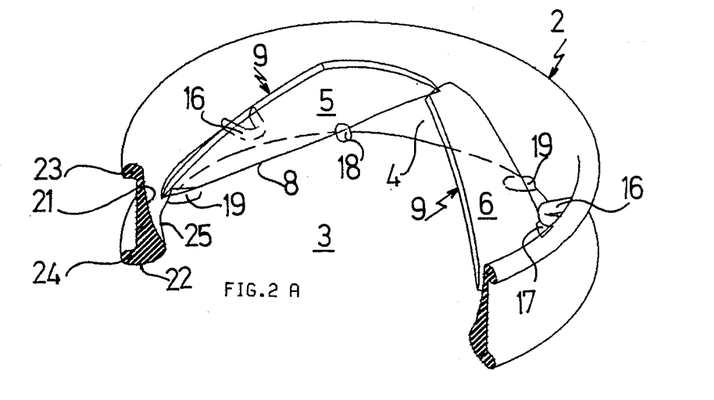

Preferably, these closure advance means are formed by magnetic masses incorporated in each flap so that the corners of two adjacent flaps have magnetic polarities of opposite signs, such as shown schematically in FIG. 2 by the signs − and + which correspond essentially to the position of the magnetic polarities which interact with each other.

These magnetic masses formed in the corners of each flap may also cooperate with additional magnetic masses which are disposed in the base between two adjacent flaps and whose dimension is substantially equal to the distance which exists between the adjacent corners of two adjacent flaps in the open position, each additional magnetic mass being disposed in the base so that its polarities correspond to the polarities of opposite sign of the magnetic masses formed in the corners of the flaps.

Figure 3A:
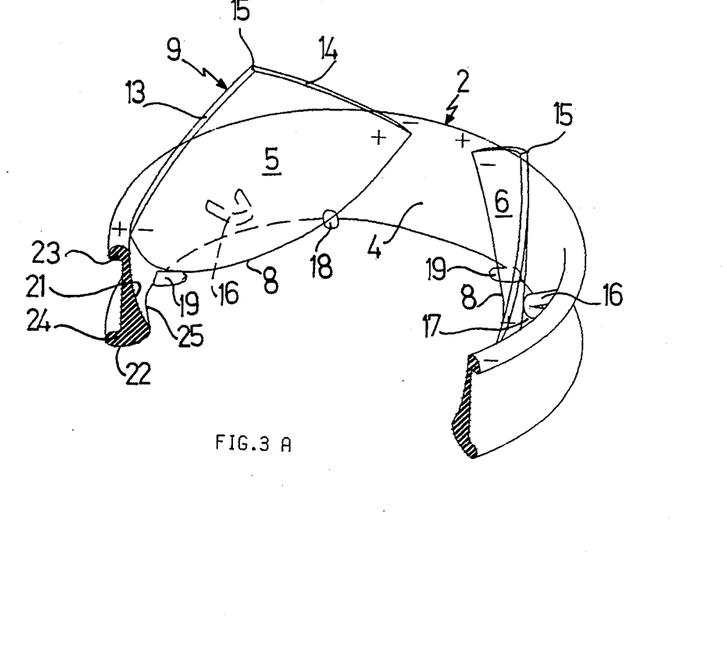

The arrangement of the additional magnetic masses is illustrated schematically in FIGS. 3 and 3a by showing essentially the position of the + and − polarities of each one.

The magnetic masses are calculated so that the attraction between the corners of adjacent flaps, for closing the valve, oppose exactly the pressure and friction forces which tend to open it when the speed of the flow in the forward direction reaches a certain percentage of its maximum value. Thus, closure of the valve will be announced before the return of the flow. The magnetic masses may be formed, in a way known per se, by small magnets fixed to the corners of the flaps by any appropriate means, or by a magnetic material incorporated during manufacture theeof in a finely dispersed form.

Insofar as the materials are concerned likely to be used for constructing the cardiac valve prosthesis, the choice is oriented towards the group of biocompatible materials such, preferably, as the material known under the trademark "PYROLYTE" because of its inertia, its wear resistance and its thrombo-resistance property (henceforth recognized) in the physiological medium, as well as titanium and materials known under their following trademarks: "DELRIN", "BIOLITE", "STELLITE" and yet others known to technicians in the matter.

When pyrolytic carbon is used, because of known mechanical requirements which prevent forming the whole of the prosthesis from such a material, it is used as a coating deposited on a substrate using a technique also known per se (cf. the American patent No. 3 526 005), the substrate being formed to the desired shape and being formed typically by graphite; in any case, the most appropriate choice of the substrate and of the thickness of the pyrolytic carbon coating are within the competence of a man skilled in the matter.

Furthermore, insofar as the formation in particular of the support base for the closure means is concerned, it is preferably to form it as a single piece avoiding, if possible, the use of a base formed by assembling several elements, for that involves the potential risks of separation of the component elements and formation of blood stagnation zones.

The one piece construction may also be envisaged, without fearing assembly problems, because the property of pyrolytic carbon may be used of being sufficiently elastically deformable to allow positioning of the closure means of the valve of the present invention, if its base and/or flaps are made from pyrolytic carbon.

Hereafter certain parts of the preceding description are taken up again so to relate them to the operation of the valve.

In the closed position, this latter opposes the reverse direction of flow by the position of the flaps which ensure sealing between these flaps, along their trailing edges and a minimum of blood leaks between their leading edge and the base of the valve.

In this position, the pressure forces on the closure means are taken up:

by the base oriented downstream of the flow in the forward direction, along the leading edge of the closure means;

by the retaining means situated between each closure means and the base.

These different bearing points, being well distributed about the closure means, ensure that the stresses are not ammplified by lever effect, as is the case when only the hinge takes up the forces.

As soon as a pressure gradient exists in the forward direction, the closurre means open naturally, since their axis of rotation is very off-centered with respect to the point of application of the pressure forces.

This movement is stopped when the corners of the closure means come to bear on the base. The impact of the closure means on the base is achieved between two solid parts and over a considerable area, which results in:

minimizing the stresses in the materials;
reducing the operating noise.

The retaining means of each closure means prevent the latter from escaping in the direction of the flow. The forces required for this function are small, for they are only produced by the forces of friction of the flow on the walls of the closure means (the pressure forces are very small for the closure means are parallel to the flow).

In the open position, the closure means are placed in the vicinity of the walls and parallel to the flow, which results in:

placing them in a part where the flow is slowed down by the proximity of the walls (viscosity effects), so in minimizing the pressure losses due to fluid friction;

avoiding the creation of vortices in the vicinity of the closure means, for they are not subjected or only very little to pressure forces since they are parallel to the flow;

leaving free of any obstacle a central part of the flow which represents more than 80% of the total passage section of the base in the preferred embodiments of the invention.

As soon as the flow direction is reversed, the friction forces which are exerted on the walls of the closure means exert a moment with respect to their axis which tends to start the closure movement. As soon as the closure means have moved through a small angle with respect to the reverse flow, pressure forces are exerted thereon which cause very rapid pivoting and closure of the valve.

If the valve is equipped with the device introducing a closure advance, such as described before, the beginning of closure due to friction forces benefits from an additional closure starting force which is obtained by the magnetic attraction of the closure means and occurs as soon as the speed of the forward flow passes below a certain value, so before reveral of the flow. In an extreme case, closure may be achieved wholly by the magnetic forces so as to be completed at the moment of reversal of the flow. In this case, the regurgitation rate would be zero. In actual fact, this case is probably not optimum for the overall efficiency of the valve, the best efficiency being related to a magnetization rate of the closure means which may be readily determined by a technician skilled in the matter.

Figure 8:
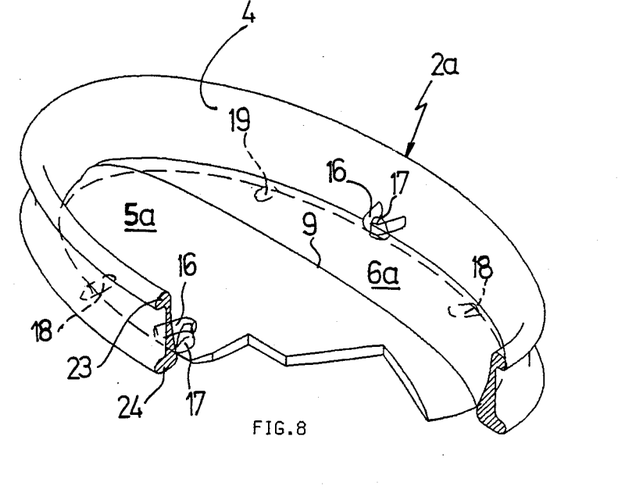
FIG. 8 shows, with parts cut away, an example of the prosthetic cardiac valve of the invention having an elliptic base.

It goes without saying that, although the description has been limited to cardiac valve prostheses of circular shape, the foregoing arrangements apply also to artifical valve of elliptic or oval shape (such as the valve illustrated in FIG. 8 whose base 2a includes two flap-valves 5a and 6a shown in the closed position) or to valves having any convex section, as well as to all the applications in which it is necessary to provide a fluid control, particularly for cryogenic fluids or others.

As is clear from the foregoing, the invention is in no manner limited to those of its embodiments, modes of construction and application which have just been described more explicitly: it embraces, on the contrary, all the variants thereof which may occur to the mind of a technician skilled in the matter, without departing from the scope and spirit of the present invention. For example, although the drawings show valves having a circular or elliptic base, it goes without saying that the prosthetic cardiac valve of the invention may have any general convex external form as well as a base whose internal wall may have a profile appropriate to the configuration adopted for each flap. Furthermore, although it is preferable to use a number of flaps greater than or equal to 2, essentially so that the valve remains of the so-called "low profile" type, it goes without saying that the guide and retaining means of the invention may be also adapted to the use of a single flap whose form may be special, particularly comparable to a shell.

In addition, though it is preferable to use a number of valves equal to 2 when the base has an elongate shape in one direction (namely tending to the oval or elliptic shape) and a number of flaps equal to 3 when the shape is circular or approximately so, it goes without saying that for a given form of the base, any number of flaps may a priori be used.

What is claimed is:

1. A prosthetic cardiac valve of the type including:

a plurality of flaps having a concave internal face and being movable, under the action of cardiac pulsations, between an open position in which they allow the blood to flow in a forward direction and a closed position in which they prevent reversal of the blood flow in a reverse direction, each closure means having two lateral corners, a leading edge and a trailing edge which converge in two corners, a base supporting the flaps and having an internal wall definng a central passage for the blood flow, as well as an upper edge and a lower edge, suture means by means of which the base is fixed to cardiac and vascular tissues, and rotational guide and retaining means for each flap between and in said open and closed positions, respectively, wherein the rotational guide and retaining means of each flap define an axis of rotation disposed at a distance from the axis of the valve which is greater than 75% of an internal radius of the base measured perpendicularly to the rotation axis of each flap, while allowing the flow between the external face of a flap and an adjacent internal wall of the base for rinsing of said guide and retaining means, the axis of rotation of each said flap being situated entirely outside the flap and being off-centered with respect to the centre of gravity of the flap so that the resultant force of the friction forces acting on the flap has, with respect to said axis during reversal of the blood flow, a sufficient moment for starting closure of said flap, and in the open position the corners of each flap bear on the internal wall of the base at zones which are situated at a distance from the axis of rotation of each said flap which is greater than 25% of an internal radius of the base measured perpendicularly to the rotation axis of each said flap, for reducing, on the one hand, the forces required for limiting opening of each said flaps and, on the other, for reducing the forces acting on the rotational guide and retaining means.

2. The prosthetic cardiac valve as claimed in claim 1, wherein said rotational guide and retaining means of each flap comprise:

a first spur which projects from the external face of the corresponding flap-valve outwardly and upwardly from the middle point of its leading edge, means about which said first spur is hinged and which is integral with the internal wall of the base, and second and third spurs which project substantially from the lower edge of the base and which are oriented towards the axis of the base, namely the flow axis, and slightly upwardly, said second and third spurs being disposed each on one side of the hinge means of said first spur and coming into contact with the leading edge and lower zone of the internal face of the corresponding flap, respectively, in the open and closed position.

3. The prosthetic cardiac valve as claimed in claim 2, wherein said hinge means of said first spur is formed by a substantially horizontal and substantially triangular stirrup which projects from the internal wall of the base and which is disposed in the lower half of this wall, in the vicinity of the median radial plane of the base, which stirrup has a radial width less than 25% of the radius of the base measured along the axis of symmetry of a flap.

4. The prosthetic cardiac valve as claimed in claim 2, wherein said hinge means of said first spur is formed by two substantially horizontal spurs which project from the internal wall of the base and which converge towards each other, the free ends of these convergent spurs being slightly spaced apart from each other and from the internal wall of the base by a radial distance less than 25% of the radius of the base measured along the axis of symmetry of a flap.

5. The prosthetic cardiac valve as claimed in claims 3 or 4, wherein the radial dimension of said hinge means of the first spur is preferably between 10% and 15% of the radius of the base measured perpendicularly to the rotation axis of each said flap.

6. The prosthetic cardiac valve as claimed in claim 1, wherein, in the open position, each flap is substantially parallel to the blood flow axis, namely the internal and external faces of each flap are lightly touched by the blood substantially parallel to the axis of the base.

7. The prosthetic cardiac valve as claimed in claim 1, wherein the internal wall of the base has in axial section a curvilinear profile which includes a concave upper portion, along which the thickness of said internal wall increases from the upper edge of the base and a lower convex portion along which the thickness of the internal wall decreases towards the lower edge of the base, said concave and convex portions of the axial profile of the internal wall of this base being separated by an annular line.

8. The prosthetic cardiac valve as claimed in claim 7, wherein the line of separation between said concave and convex portions of said axial profile of the internal wall of the base varies, in a zone between two adjacent flaps, along a radial profile which is projecting with respect to the radial profile of the median zone of the flap and which is essentially symmetrical with respect to the trailing edges of two adjacent flaps touching each other in the closed position, the leading edge of each flap having in its turn a profile matching said separating line between said concave and convex portions of the profile of the internal wall of the base, namely the leading edge of each flap has a central convex portion and two lateral re-entrant portions, these latter matching in the closed position said projecting radial profile of the internal wlal of the valve, matching in the closed position between the leading edge of each flap and the internal wall of the base being achieved so as to reduce the leaks of blood to a minimum.

9. The prosthetic cardiac valve as claimed in claim 8, wherein the portion of said separation line between said concave and convex portions of the axial profile of the internal wall of the base, which corresponds to the convex portion of the leading edge of each flap, is situated at a distance from the lower edge of the base which is equal to about 10% of the height of the base, whereas the middle point of the portion of said separation line with radial projecting profile which corresponds to the two concave portions of two adjacent flaps is situated at a distance from the lower edge of the base which is equal to about 20% of its height, the passage between said two portions of said separation line being progressive.

10. The prosthetic cardiac valve as claimed in claim 1, wherein each flap has at the level of its corners which come into contact with the internal wall of the base in the closed position and on its external face a reinforcement thickening allowing the contact to be made by a surface and not by a point or line, thus limiting the contact pressure and so the wear as well as the operating noise.

11. The prosthetic cardiac valve as claimed in claim 1, wherein each of the flaps is provided with closure advance means, namely means intended to anticipate closure of the flaps on the return of the blood flow in the reverse direction, which cooperate with the closure starting means formed by said virtual off-centered axes.

12. The prosthetic cardica valve as claimed in claim 11, wherein said closure advance means are formed by magnetic masses of opposite polarities formed at the level of the corners of each flap, the magnetic polarities of the corners of two adjacent flaps being opposite.

13. The prosthetic cardicac valve as claimed in claim 12, wherein said magnetic masses formed at the level of the corners of each flap cooperate with additional magnetic masses which are disposed in the base between two adjacent flaps and whose dimension is substantially equal to the distance which exists between the adjacent corners of two adjacent flaps in the open position, each additional magnetic mass being disposed in the base so that its polarities correspond to the polarities of opposite sign of the magnetic masses formed in the corners of the flaps.

14. The prosthetic cardiac valve as claimed in claim 12 wherein said magnetic masses are formed by small magnets.

15. The prosthetic cardiac valve as claimed in claim 12 or 13, wherein said magnetic masses are formed by a magnetic material incorporated during manufacture of each flap or of the base.

16. The prosthetic cardiac valve as claimed in claim 1, wherein the base is circular or substantially circular.

17. The prosthetic cardiac valve as claimed in claim 1, characterized in that the base is elliptic or substantially ellpitic.

18. The prosthetic cardiac valve as claimed in claim 1, wherein the number of flaps is equal to 2.

19. The prosthetic cardiac valve as claimed in claim 1, wherein the number of flaps is greater than 2.

20. The prosthetic cardiac valve as claimed in claim 19, wherein the number of flaps is preferably equal to 3.

21. A prosthetic cardiac valve as set forth in claim 1 wherein a profile of each closure means varies from an axis of each said closure means towards at least one of said two lateral corners and parallel to said axis of each said closure means.

* * * * *